United States Patent
Yoon et al.

(10) Patent No.: US 12,011,589 B2
(45) Date of Patent: Jun. 18, 2024

(54) SYSTEM AND METHOD FOR PLANNING ELECTRIC FIELD CANCER TREATMENT BASED ON ABSORBED ENERGY

(71) Applicants: FIELDCURE CO., LTD., Seoul (KR); KOREA UNIVERSITY RESEARCH AND BUSINESS FOUNDATION, Seoul (KR)

(72) Inventors: Myong Geun Yoon, Gyeonggi-do (KR); Geon Oh, Seoul (KR); Jong Hyun Kim, Seoul (KR)

(73) Assignees: FIELDCURE CO., LTD., Seoul (KR); KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 650 days.

(21) Appl. No.: 17/259,492

(22) PCT Filed: Jul. 20, 2020

(86) PCT No.: PCT/KR2020/009527
§ 371 (c)(1),
(2) Date: Jan. 11, 2021

(87) PCT Pub. No.: WO2022/014761
PCT Pub. Date: Jan. 20, 2022

(65) Prior Publication Data
US 2022/0184391 A1   Jun. 16, 2022

(30) Foreign Application Priority Data
Jul. 16, 2020   (KR) .................. 10-2020-0088365

(51) Int. Cl.
*A61N 1/36* (2006.01)
*A61N 1/08* (2006.01)
(Continued)

(52) U.S. Cl.
CPC .......... *A61N 1/36002* (2017.08); *A61N 1/08* (2013.01); *A61N 1/40* (2013.01); *G06T 7/11* (2017.01);
(Continued)

(58) Field of Classification Search
CPC ........ A61N 1/36002; A61N 1/08; A61N 1/40; A61N 1/0476; A61N 1/36034; G06T 7/11;
(Continued)

(56) References Cited

U.S. PATENT DOCUMENTS

2004/0176804 A1   9/2004   Palti
2010/0030211 A1   2/2010   Davalos et al.
(Continued)

FOREIGN PATENT DOCUMENTS

KR   10-2016-0076703   7/2016
KR   10-1721798   3/2017
(Continued)

OTHER PUBLICATIONS

Eilon D. Kirson et al., "Disruption of cancer cell replication by alternating electric fields", Cancer Research, 64, 3288-3295 (2004).
(Continued)

*Primary Examiner* — Santiago Garcia (57) ABSTRACT

The present disclosure provides a system for planning electric field cancer treatment based on absorbed energy including: an image classification unit to classify a patient's medical image into an organ and a tumor; a property information setting unit to set property information for each region classified by the image classification unit; a prescription information determination unit to set a prescription method; a dose calculation unit to initially set the number and location of electrodes used for electric field cancer treatment and the electric field intensity for each electrode;
(Continued)

and a dose optimization unit to optimize the dose by changing at least one electrode.

13 Claims, 7 Drawing Sheets

(51) Int. Cl.
*A61N 1/40* (2006.01)
*G06T 7/11* (2017.01)

(52) U.S. Cl.
CPC ............... *G06T 2207/10081* (2013.01); *G06T 2207/10088* (2013.01); *G06T 2207/20081* (2013.01); *G06T 2207/30096* (2013.01)

(58) Field of Classification Search
CPC . G06T 2207/10081; G06T 2207/10088; G06T 2207/20081; G06T 2207/30096; A61B 5/0036; A61B 5/055; A61B 5/4836; A61B 5/7264; A61B 5/0537; A61B 6/032; A61B 6/5217
See application file for complete search history.

(56) References Cited

U.S. PATENT DOCUMENTS

| | | | |
|---|---|---|---|
| 2014/0330268 | A1* | 11/2014 | Palti .................. A61P 35/00 606/34 |
| 2017/0120041 | A1 | 5/2017 | Wenger et al. |
| 2018/0318393 | A1* | 11/2018 | Pierce .................. A61N 1/327 |
| 2019/0314631 | A1 | 10/2019 | Wong et al. |
| 2019/0336757 | A1* | 11/2019 | Rodriguez ......... A61B 18/1477 |
| 2020/0219261 | A1 | 7/2020 | Shamir et al. |
| 2020/0368525 | A1* | 11/2020 | Maag ................. A61N 1/36002 |
| 2022/0230310 | A1* | 7/2022 | Xie ...................... G06V 10/758 |

FOREIGN PATENT DOCUMENTS

| | | |
|---|---|---|
| KR | 10-2020-0004228 | 1/2020 |
| WO | WO 2017-072706 | 5/2017 |
| WO | WO 2019-148268 | 8/2019 |

OTHER PUBLICATIONS

Miklos Pless, Uri Weinberg, "Tumor treating fields: concept, evidence, future", Expert Opinion, 20(8), 1099-1106 (2011).

Angela M. Davies et al., "Tumor treating fields: a new frontier in cancer therapy", Annals of the New York academy of sciences, 1291, 86-95 (2013).

Stupp et al., "Effect of Tumor-Treating Fields Plus Maintenance Temozolomide vs Maintenance Temozolomide Alone on Survival in Patients With Glioblastoma: A Randomized Clinical Trial", Journal of the American Medical Association, 318(23), 2306-2316 (2017).

Eilon D. Kirson et al., "Alternating electric fields (TTFields) inhibit metastatic spread of solid tumors to the lungs", Clin Exp Metastasis 26, 633-640 (2009).

Novocure Corporate Presentation (https://3sj0u94bgxp33grbz1fkt62h-wpengine.netdna-ssl.com/wp-content/uploads/2019/05/201905_NVCR_Corporate_Presentation_vFF.pdf).

Eilon D. Kirson et al., "Alternating electric fields arrest cell proliferation in animal tumor models and human brain tumors", PNAS, 104(24), 10152-10157 (2007).

Yunhui Jo et al., "Effectiveness of a Fractionated Therapy Scheme in Tumor Treating Fields Therapy", Technology in Cancer Research & Treatment,18, 1-10 (2019).

Denise Fabian et al., "Treatment of Glioblastoma (GBM) with the Addition of Tumor-Treating Fields (TTF): A Review", Cancers, 11, 174 (2019).

Matthew T. Ballo et al., "Correlation of Tumor Treating Fields Dosimetry to Survival Outcomes in Newly Diagnosed Glioblastoma: A Large-Scale Numerical Simulation-Based Analysis of Data from the Phase 3 EF-14 Randomized Trial", Int J Radiation Oncol Biol Phys, vol. 104, No. 5, pp. 1106-1113 (2019).

Dimitris J. Panagopoulos et al., "Evaluation of Specific Absorption Rate as a Dosimetric Quantity for Electromagnetic Fields Bioeffects", PLoS One, 8(6), e62663 (2013).

Stefano Mandija et al., "Opening a new window on MR-based Electrical Properties Tomography with deep learning", Scientific Reports, 9, 8895 (2019).

International Search Report dated Apr. 13, 2021 for PCT/KR2020/009527.

Hershkovich, H. S. et al., Power Density Loss and Related Measures can be used to Quantify the Dose of Tumor Treating Fields (TTFields), International Journal of Radiation Oncology Biology Physics, vol. 102, No. 3, Supplement, 2018, e533.

European Search Report dated Nov. 25, 2022 for European Patent Application No. 20829173.2 (Publication No. 3967365), 10 pages.

Office Action dated Oct. 25, 2022 corresponding to Japanese Application No. 2021-502968, 2 pages.

Office Action dated Aug. 26, 2022 corresponding to Korean Application No. 10-2020-0088365, 4 pages.

\* cited by examiner

SYSTEM AND METHOD FOR PLANNING ELECTRIC FIELD CANCER TREATMENT BASED ON ABSORBED ENERGY

This application claims the priority of Korean Patent Application No. 10-2020-0088365, filed on Jul. 16, 2020 in the KIPO (Korean Intellectual Property Office), the disclosure of which is incorporated herein entirely by reference. Further, this application is the National Stage application of International Application No. PCT/KR2020/009527, filed Jul. 20, 2020, which designates the United States and was published in Korean. Each of these applications is hereby incorporated by reference in their entirety into the present application.

TECHNICAL FIELD

The present disclosure relates to a system and method for planning electric field cancer treatment based on absorbed energy, particularly when the physically absorbed energy delivered to each tissue in the body is calculated based on the intensity of electric fields applied to these tissues, on the density and electrical conductivity of tissues, and on the electric field duration. In this system, the dose prescribed for each patient is determined based on the calculated absorbed energy; a treatment plan is formulated such that the maximal prescribed dose is delivered to the tumor and minimal doses are delivered to the surrounding normal tissues, allowing treatment to be performed based on the treatment plan.

BACKGROUND ART

In the early 2000s, the application of alternating current electric fields to dividing cancer cells was found to delay cell division or induce cell death, and the first study applying this phenomenon to cancer treatment was published soon after (Non-Patent Literature 1). Many subsequent studies have assessed the safety and efficacy of electric field cancer treatment.

Electric field treatment was found to have three important benefits. First, because electric fields only affect dividing cells, electric fields intensively affect cancer cells, which divide faster than normal cells, suggesting that this treatment would have fewer side effects than existing therapy (Non-Patent Literature 2). Further investigations, published in 2013, showed that of nine side effects, seven were lower with electric field treatment than with standard anticancer therapy, whereas the other two were nearly equivalent (Non-Patent Literature 3).

A second benefit of electric field treatment is that, although cancer treatment using this method is still in its initial stage, it shows better efficacy than existing therapy. For example, standard anticancer treatment of patients with glioblastoma multiforme (GBM), a brain cancer with a very low cure rate, resulted in a median progression free survival (PFS) of 4.0 months, a median overall survival (OS) of 16.0 months, and a 2-year survival probability of 31%. The addition of electric field treatment resulted in a median PFS and OS of 6.7 and 20.9 months, respectively, and a 2-year survival probability of 43% (Non-Patent Literature 4).

A third benefit of electric field treatment is that the application of electric fields over a wide area, including a target site, would have an effect on tumors too small to visualize by imaging methods such as computed tomography (CT). When electric fields are applied to a tumor, non-negligible electric fields are also applied to regions around the tumor, thus affecting micro-tumors near the main tumor. This would suppress the division of cancer cells in micro-tumors, dramatically reducing the transition probability of the disease progressing from one site to another (Non-Patent Literature 5).

Electric field therapy was approved by the U.S. Food and Drug Administration (FDA) for the treatment of recurrent glioblastoma in 2011 and newly diagnosed glioblastoma in 2015 and has received a CE mark in Europe. At present, electric field treatment is used in about 1000 hospitals in the USA, Germany and Switzerland, and has been approved in Japan for the treatment of patients with recurrent glioblastoma. Additionally, the number of patients receiving treatment is rapidly increasing every year, with 152 patients receiving electric field therapy in 2014 and 8813 in 2018, a greater than 50-fold increase over 4 years (Non-Patent Literature 6).

However, current electric field cancer treatment has several drawbacks, requiring efforts to maximize the treatment effect.

For example, the effects of electric field treatment on cancer cells are dependent on the intensity and duration of the electric fields applied to tissues. Specifically, increasing the intensity and/or duration of electric fields proportionately increases rates of cancer cell death and suppression of their division (Non-Patent Literature 7 and 8).

Current commercially available electric field cancer treatment systems apply electric fields such that their intensity is below the maximum intensity that has no side effects on skin. Moreover, treatment duration should be 18-24 hours/day, limited only by patient tolerance (Non-Patent Literature 7 and 9).

Thus, the intensity and duration of current electric field treatment suitable for the treatment of a specific tumor have not been predefined. Rather, treatment consists of the application of electric fields of maximum intensity for the maximum treatment duration within the range in which side effects do not occur. That is, electric field treatment does not introduce the concept of dose commonly used in radiation therapy or anticancer therapy, and does not vary prescribed doses that depend on the type or condition of the tumor.

However, treatment without prescribed doses makes it impossible to determine the intensity and duration of electric fields to be applied to a tumor or to determine their relative importance and effects. Although treatment effects are likely proportional to the intensity and duration of electric fields, it is impossible to accurately determine whether these relationships are linear or more complex. Accordingly, it is impossible to optimize an electric field treatment plan and to effectively treat the patient.

A study of electric field treatment in 340 patients with brain tumors found that prognosis was much better when power loss density in the tumor was >0.77 mW/cm$^3$ than <0.77 mW/cm$^3$ (Non-Patent Literature 10). Although power loss density is considered only one criterion in determining prescribed doses for electric field treatment, its use in determining electric field treatment has a critical limitation. Specifically, although the percentage of cancer cells killed is proportional to the duration of electric field treatment, power loss density is unrelated to treatment duration (Non-Patent Literature 8).

Additionally, different cells in various types of cancers respond differently to electric field treatment, with response depending on the frequency of the applied electric fields (Non-Patent Literature 7). Accordingly, the effects on cells of the applied electric fields may be determined by physical quantities related to the intensity and duration of the electric fields, as well as the biological effects that depend on the applied frequency.

Although power loss density may be suitable for predicting the prognosis of patients who receive electric field treatment, there are limitations in using power loss density as the dose unit for electric field treatment. Rather, a new concept is required for determining doses of electric field treatment based on electric field duration and frequency.

Non-Patent Literature (Non-Patent Literature 1) Eilon D. Kirson et al, disruption of cancer cell replication by alternating electric fields, cancer research, 64, 3288-3295 (2004)

(Non-Patent Literature 2) Miklos Pless, Uri Weinberg, tumor treating fields: concept, evidence, future, Expert Opinion, 20(8), 1099-1106 (2011)

(Non-Patent Literature 3) Angela M. Davies et al, Tumor treating fields: a new frontier in cancer therapy, Annals of the New York academy of sciences, 1291, 86-95 (2013)

(Non-Patent Literature 4) Stupp et al, Effect of Tumor-Treating Fields Plus Maintenance Temozolomide vs Maintenance Temozolomide Alone on Survival in Patients With Glioblastoma: A Randomized Clinical Trial, Journal of the American Medical Association, 318(23), 2306-2316 (2017)

(Non-Patent Literature 5) Eilon D. Kirson et al. Alternating electric fields (TTFields) inhibit metastatic spread of solid tumors to the lungs, Clin Exp Metastasis 26, 633-640 (2009)

(Non-Patent Literature 6) Novocure Corporate Presentation (https://3sj0u94bgxp33grbz1fkt62h-wpengine.netdna-ssl.com/wp-content/uploads/2019/05/201905_NVCR_Corporate_Presentation_vFF.pdf)

(Non-Patent Literature 7) Eilon D. Kirson et al, alternating electric fields arrest cell proliferation in animal tumor models and human brain tumors, PNAS, 104 (24), 10152-10157 (2007)

(Non-Patent Literature 8) Yunhui Jo et al, Effectiveness of a Fractionated Therapy Scheme in Tumor Treating Fields Therapy, Technology in Cancer Research & Treatment, 18, 1-10 (2019)

(Non-Patent Literature 9) Denise Fabian et al, Treatment of Glioblastoma (GBM) with the Addition of Tumor-Treating Fields (TTF): A Review, Cancers, 11, 174 (2019)

(Non-Patent Literature 10) Matthew T. Ballo et al, Correlation of Tumor Treating Fields Dosimetry to Survival Outcomes in Newly Diagnosed Glioblastoma: A Large-Scale Numerical Simulation-Based Analysis of Data from the Phase 3 EF-14 Randomized Trial, Int J Radiation Oncol Biol Phys, Vol. 104, No. 5, pp. 1106-1113 (2019)

(Non-Patent Literature 11) Dimitris J. Panagopoulos et al, Evaluation of Specific Absorption Rate as a Dosimetric Quantity for Electromagnetic Fields Bioeffects, PLoS One, 8(6), e62663 (2013)

(Non-Patent Literature 12) Stefano Mandija et al. Opening a new window on MR-based Electrical Properties Tomography with deep learning, Scientific Reports, 9, 8895 (2019)

DISCLOSURE OF THE INVENTION

Technical Problem

Accordingly, this technical field is required to set the dose criteria for electric field treatment to maximize the treatment effect and minimize the side effects. A treatment plan for each patient should be designed, such that the maximal prescribed dose is delivered to a tumor and a minimal dose delivered to surrounding normal tissues. This requires the introduction of a dose unit for electric field treatment, with treatment performed using the calculated parameters in conjunction with electric field treatment equipment.

The objective of the present disclosure is not limited to the above-mentioned objective. Other objectives not mentioned herein will be clearly understood by those familiar with this field, based on the description shown below.

Technical Solution

To solve the above-described problem, an embodiment of the present disclosure provides a system for planning electric field cancer treatment based on absorbed energy.

This system may include an image classification unit to classify a patient's medical image into organs and tumors; a medical image that includes the organs and tumors; a property information setting unit to set property information for each region classified by the image classification unit; a prescription information determination unit to set a prescription method, taking into account input type and condition information of the tumor, and to determine prescription information, including prescribed doses, treatment times, treatment duration and treatment frequency; a dose calculation unit to determine the number of electrodes used initially for electric field cancer treatment and to determine the location and electric field intensity of each electrode (i.e., the voltage applied to each electrode), based on the location of each region classified by the image classification unit, and to calculate a dose distribution in the body based on the initial settings; and a dose optimization unit to optimize doses by changing at least the number, location or electric field intensity of at least one electrode such that the maximal prescribed dose is delivered to the tumor and a minimal dose is delivered to surrounding normal tissues.

An additional embodiment of the present disclosure provides a method for planning electric field cancer treatment based on absorbed energy.

This method may include segmenting a region of interest (ROI) including a tumor and an organ in a patient's medical image; determining a method of dose prescription as an absorbed energy density based approach or a specific energy absorbed based approach; determining the prescription information, including the prescribed dose, treatment times, treatment duration and treatment frequency, according to the set prescription method; calculating the dose distribution in the body based on the number and location of electrodes and the initially set electric field intensity for each electrode, based on the tumor and organs; and evaluating and optimizing a treatment plan based on the calculated dose distribution in the body.

The above-described technical solution does not enumerate all the features of the present disclosure. Various features of the present disclosure and their advantages and effects will be better understood in more detail by reference to the following specific embodiments.

Advantageous Effects

According to an embodiment of the present disclosure, the dose of electric field treatment can be set by regarding the absorbed energy as being substantially proportional to its inhibition of cell proliferation when electric fields are applied to dividing cells. These settings can be used to determine the clinically prescribed dose applicable to the treatment of each tumor. This may enable the formulation and evaluation of a systematic treatment plan that was previously impossible due to the absence of a dose unit for electric field treatment.

Further, the treatment plan can be formulated such that the prescribed dose is optimized in the human body and the calculated parameters are applied to the equipment utilized for electric field treatment such that the maximum prescribed dose is delivered to the tumor and minimal doses are delivered to surrounding normal tissues.

In addition, the effects of electric field cancer treatment can be maximized by setting reasonable prescribed doses for the treatment of patients through statistical analysis of the clinical results.

The effect of the present disclosure is not limited to the above-mentioned effects. Other effects not mentioned herein will likely be understood by those familiar with this field, based on the description shown below.

BEST MODE FOR CARRYING OUT THE INVENTION

Hereinafter, the preferred embodiments will be described in detail with reference to the accompanying drawings to allow those having ordinary skill in the technical field pertaining to the present disclosure to easily practice the present disclosure. However, in describing these preferred embodiments in detail, certain detailed descriptions of relevant known functions or elements that may make the key subject matter unnecessarily ambiguous are omitted. Additionally, the same sign is used for elements having similar functions and roles throughout the entire drawing.

Throughout the specification, elements described as being connected to one another may either be directly connected or indirectly connected through intervening elements. In addition, unless the context clearly indicates otherwise, the word 'comprising' specifies the presence of stated elements but does not preclude the presence or addition of one or more other elements.

Prior to describing a system and method for planning electric field cancer treatment based on absorbed energy according to an embodiment of the present disclosure, the criteria for quantitating the inhibitory effect of electric field treatment on cell proliferation is described in detail.

Cell viability was assessed after electric fields of intensity ~1 V/cm and frequency of 150 kHz were applied to cells of the malignant glioma cell line U373 (FIGS. 1 to 3) and compared with the viability of control, untreated cells, by cell counting. The mean of three experiments was calculated, and the ability of electric fields to inhibit cell proliferation was calculated using Equation 1.

$$\text{Inhibition of cell proliferation (\%)} = (1 - \text{Number of cells in the test group/Number of cells in the control}) \times 100 \quad \text{[Equation 1]}$$

For example, when the number of living cells in the test group subjected to electric fields was 70% of the number in the control group, treatment inhibited cell proliferation 30% relative to control.

Figure 1:
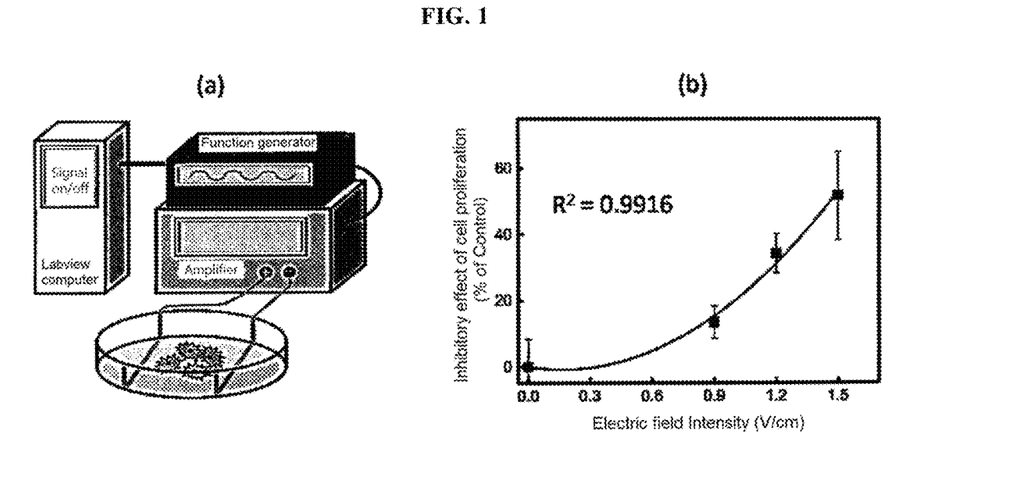
FIG. 1 is a diagram showing the inhibitory effect of electric field treatment on cell proliferation as a function of electric field intensity.

FIG. 1 shows the inhibitory effect of electric fields on cell proliferation as a function of electric field intensity. FIG. 1(a) shows the configuration of an instrument used to assess the inhibition of cell proliferation by a 150 kHz alternating current electric field, and FIG. 1(b) is a graph showing the inhibition of cell proliferation as a function of electric field intensity. This graph shows that the inhibition of cell proliferation increases with the applied electric field intensity, with this relationship being closer to a nonlinear rather than a simple linear relationship. The curve shown in FIG. 1(b) is the result of fitting data to a curve in two dimensions, with a determination coefficient $R^2$ of 0.9916.

Figure 2:
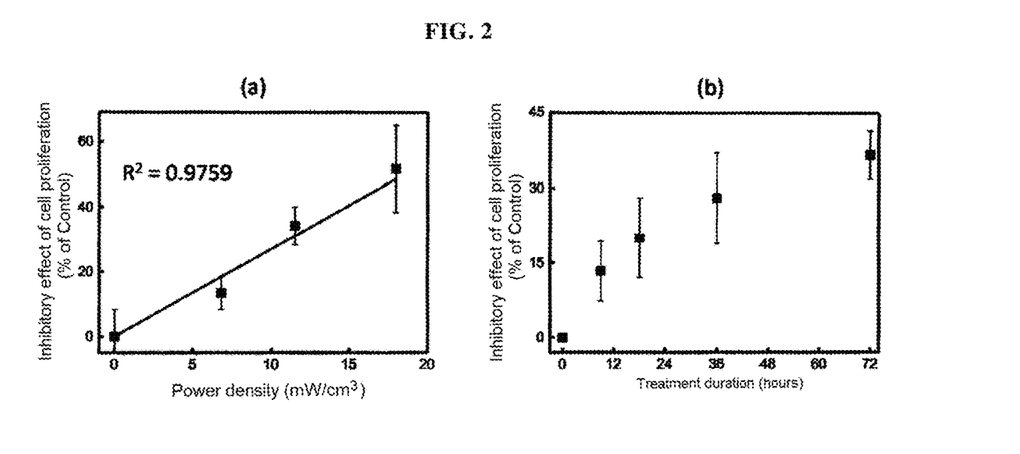
FIG. 2 is a diagram showing the inhibitory effect of electric field treatment on cell proliferation as a function of power loss density and electric field duration.

FIG. 2 is a diagram showing the inhibitory effects of electric fields on cell proliferation as a function of power loss density and electric field duration. FIG. 2(a) is a graph showing the relationship between power loss density and inhibition of cell proliferation following application of a 150 kHz alternating current electric field, and FIG. 2(B) is a graph showing the relationship between electric field (treatment) duration and inhibition of cell proliferation when the power loss density was fixed at 11.5 mW/cm³.

FIG. 2(b) shows that the inhibition of cell proliferation was proportional to power loss density, defined as ½ σE², where σ is electrical conductivity and E is electric field intensity. The curve shown in FIG. 2(a) is the result of fitting data to a curve in one dimension.

Evaluation of both FIG. 1(b) and FIG. 2(a) shows that the ability of electric fields to inhibit cell proliferation is directly proportional to the square of the electric field intensity rather than the electric field intensity, and thus is more linearly proportional to power loss density, with a determination coefficient $R^2$ of 0.9759.

FIG. 2(b) shows that the ability of electric fields to inhibit cell proliferation is proportional to the electric field duration.

Figure 3:
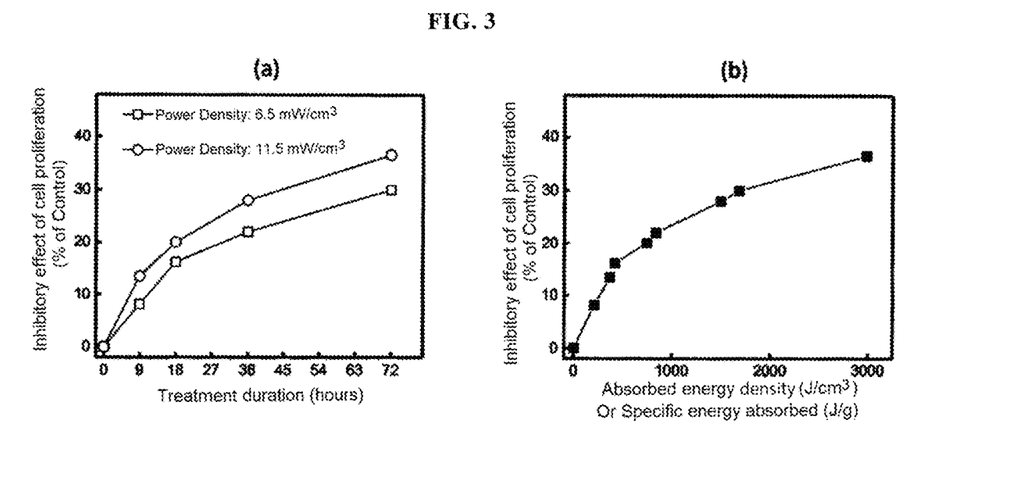
FIG. 3 is a diagram showing the inhibitory effect of electric field treatment on cell proliferation in a patient in response to changes in power loss densities and electric field durations.

FIG. 3 shows the combined effects of power loss densities and different field durations on the inhibition of cell proliferation. FIG. 3(a) shows the inhibitory effects of electric fields on cell proliferation as a function of electric field duration at power loss densities of 6.5 mW/cm$^3$ and 11.5 mW/cm$^3$, whereas FIG. 3(b) shows the inhibitory effects of electric fields on cell proliferation as a function of absorbed energy per unit volume or unit mass.

FIG. 3(a) shows that, when electric field durations were equal, a higher power loss density had a greater inhibitory effect on cell proliferation.

FIG. 3(b) shows a relationship between the inhibition of cell proliferation and the absorbed energy density (i.e., absorbed energy per unit volume) or specific energy absorbed (i.e., absorbed energy per unit mass), with absorbed energy density calculated as shown in Equation 2 and specific energy absorbed calculated as shown in Equation 3.

Absorbed energy density=power loss density×electric field duration [Equation 2]

Specific energy absorbed=(power loss density×electric field duration)÷(mass density) [Equation 3]

The inhibition of cell proliferation was found to be proportional to the absorbed energy density or specific energy absorbed (FIG. 3(b)). The absorbed energy transmitted to the cells, a parameter that includes power loss density and electric field duration, is proportional to the inhibition of cell proliferation. This parameter may be a more practical and reasonable criterion for quantitating the effect of electric fields on cell proliferation than power loss density in the absence of electric field duration. The difference between absorbed energy density and specific energy absorbed is based on whether the mass per unit volume is taken into account, and both may be used as the criteria for quantitating the inhibitory effect of electric fields on cell proliferation (Non-Patent Literature 7, 8, 10).

Figure 4:
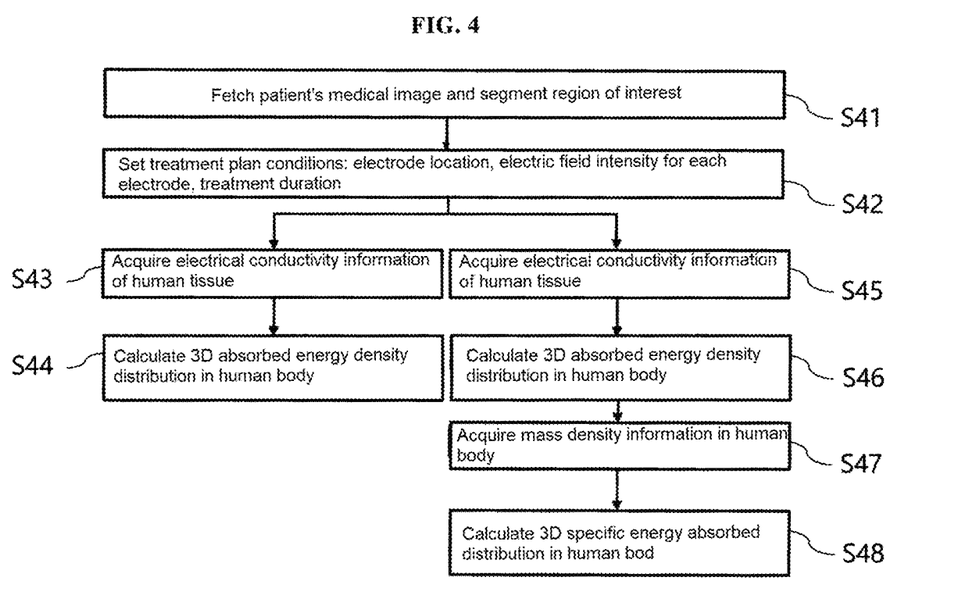
FIG. 4 is a diagram showing the process of calculating the distribution of absorbed energy density or specific energy absorbed in the body based on the medical image of a patient undergoing electric field treatment.

FIG. 4 is a diagram showing the process of calculating the distribution of absorbed energy density or specific energy absorbed in the body using a medical image for a patient undergoing electric field treatment.

Medical images of patients may be retrieved and a region of interest (ROI) segmented (S41). Treatment plan conditions (for example, the location and electric field intensity of each electrode, and treatment duration) may be set (S42).

Subsequently, to calculate the absorbed energy density distribution, electrical conductivity information of each human tissue may be acquired (S43), and a 3-dimensional (3D) absorbed energy density distribution in the body may be calculated according to Equation 2, above (S44). Electrical conductivity information of each human tissue can also be used to calculate the specific energy absorbed distribution (S45). The 3D absorbed energy density distribution can also be calculated according to Equation 2, above (S46). Based on the mass density information of each human tissue (S47), the 3D specific energy absorbed distribution in the human body can be calculated by dividing the absorbed energy density by the mass density of each human tissue (S48).

Figure 5:
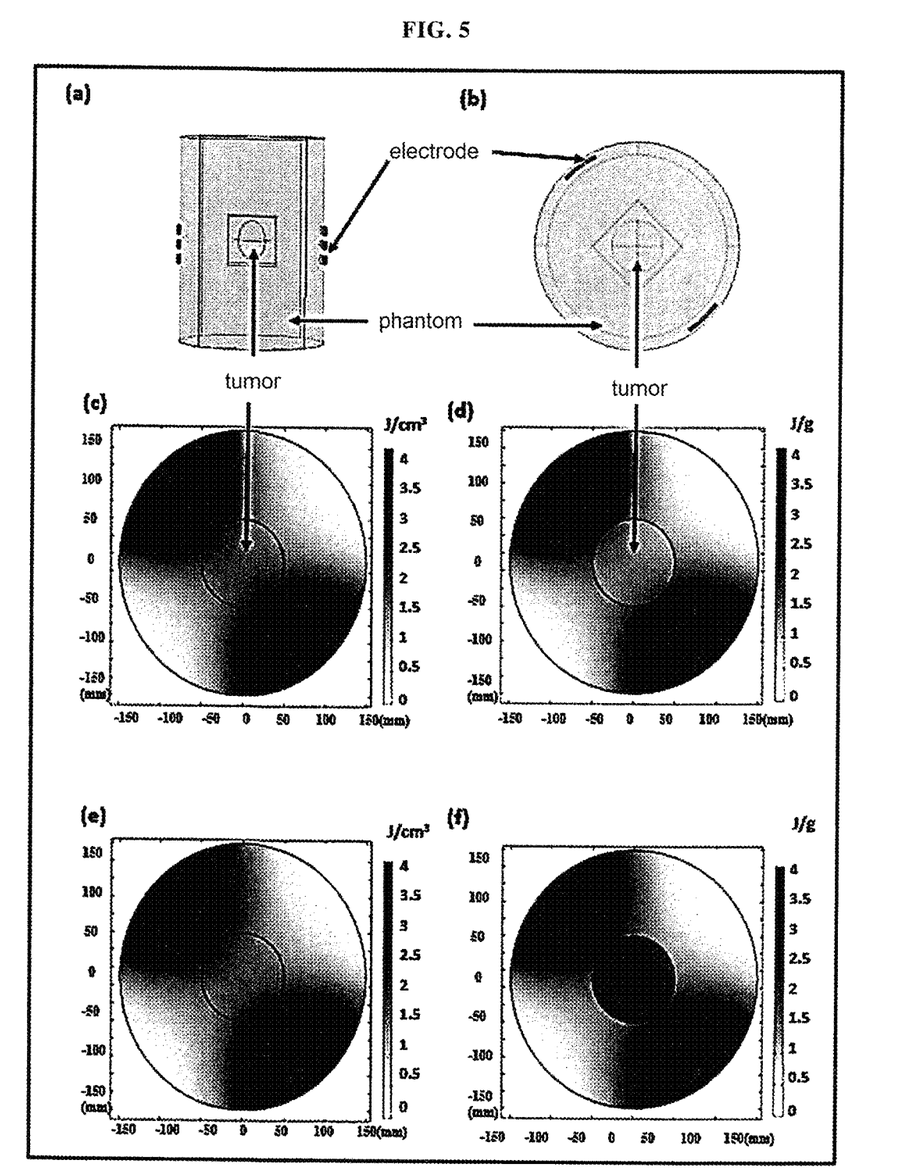
FIG. 5 is a diagram showing the distribution of absorbed energy density and specific energy absorbed when electric fields of 200 kHz were applied to a patient with tumor mass densities of 1.2 g/cm3 and 0.6 g/cm3, based on the assumption that the mass density of normal tissues in a human model phantom is 1 g/cm3.

FIG. 5 shows the distribution of absorbed energy density and specific energy absorbed when electric fields of 200 kHz are applied to a patient with a mass density of the tumor of 1.2 g/cm$^3$ and 0.6 g/cm$^3$, whereas the mass density of normal tissues in a human model phantom is 1 g/cm$^3$. FIGS. 5(a) and 5(b) show the coronal and axial planes of the human model phantom, respectively. FIGS. 5(c) and 5(d) show the distributions of absorbed energy density (J/cm$^3$) and of specific energy absorbed (J/g), respectively, when the mass density of the tumor is 1.2 g/cm$^3$, and FIGS. 5(e) and 5(f) show the distributions of absorbed energy density (J/cm$^3$) of specific energy absorbed (J/g), respectively, when the mass density of the tumor is 0.6 g/cm$^3$.

Tumors with a mass density of 1.2 g/cm$^3$ differ little from the surrounding normal tissues, which have a mass density of 1 g/cm$^3$, resulting in similar distributions of absorbed energy density and specific energy absorbed in tumors and normal tissue (FIGS. 5(c) and (d)). In contrast, tumors with a mass density of 0.6 g/cm$^3$ differ more from the surrounding normal tissues, which have a mass density of 1 g/cm$^3$, resulting in noticeably different distributions of absorbed energy density and specific energy absorbed by tumors and normal tissues (FIGS. 5(e) and (f)).

These findings show that, as the difference in mass density between a tumor and surrounding normal tissues becomes larger, so do the distributions of absorbed energy density and specific energy absorbed. These findings suggest that it may be necessary to select a specific absorbed energy density or specific energy absorbed for consistent use as a dosage unit.

Figure 6:
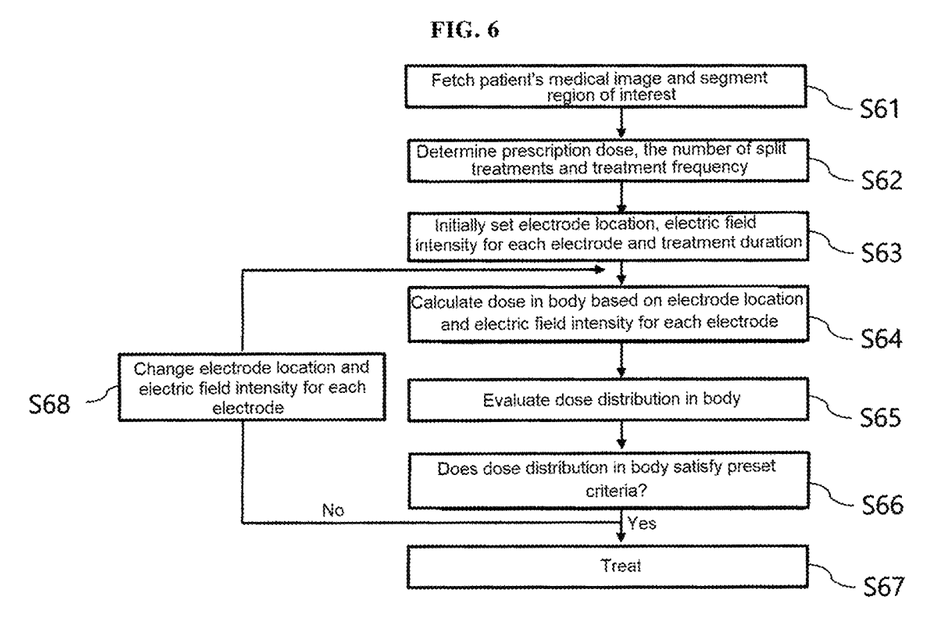
FIG. 6 is a diagram showing the process of optimizing the dose in a body using the absorbed energy based dose unit when creating an electric field treatment plan.

FIG. 6 is a diagram showing a process for optimizing the dose in the body using the absorbed energy based dose unit when creating an electric field treatment plan. After retrieving the patient's medical image and segmenting an ROI (S61), prescription information, including the prescribed dose, the number of split treatments (e.g., the daily treatment duration and the total treatment days) and the treatment frequency may be determined (S62). The prescribed dose may be based on absorbed energy density or specific energy absorbed.

After determining the electrode locations, the electric field intensity for each electrode (i.e., the voltage applied to each electrode) and the treatment duration are initially set (S63). The electric field dose in the body may be calculated based on the settings (S64), and the calculated electric field dose distribution in the body may be evaluated (S65). This allows determination of whether the preset criteria have been satisfied (S66).

If the calculated electric field dose distribution in the body does not satisfy the preset criteria, the location of at least one electrode or the electric field intensity for each electrode must be changed (S68). The optimization process should be repeatedly performed, until the electric field dose distribution in the body satisfies the preset criteria (S64 to S66).

This optimization process enables treatment to be performed such that a maximum dose (i.e., absorbed energy density or specific energy absorbed) is delivered to the tumor and a minimal dose to surrounding normal tissues (S67).

Figure 7:
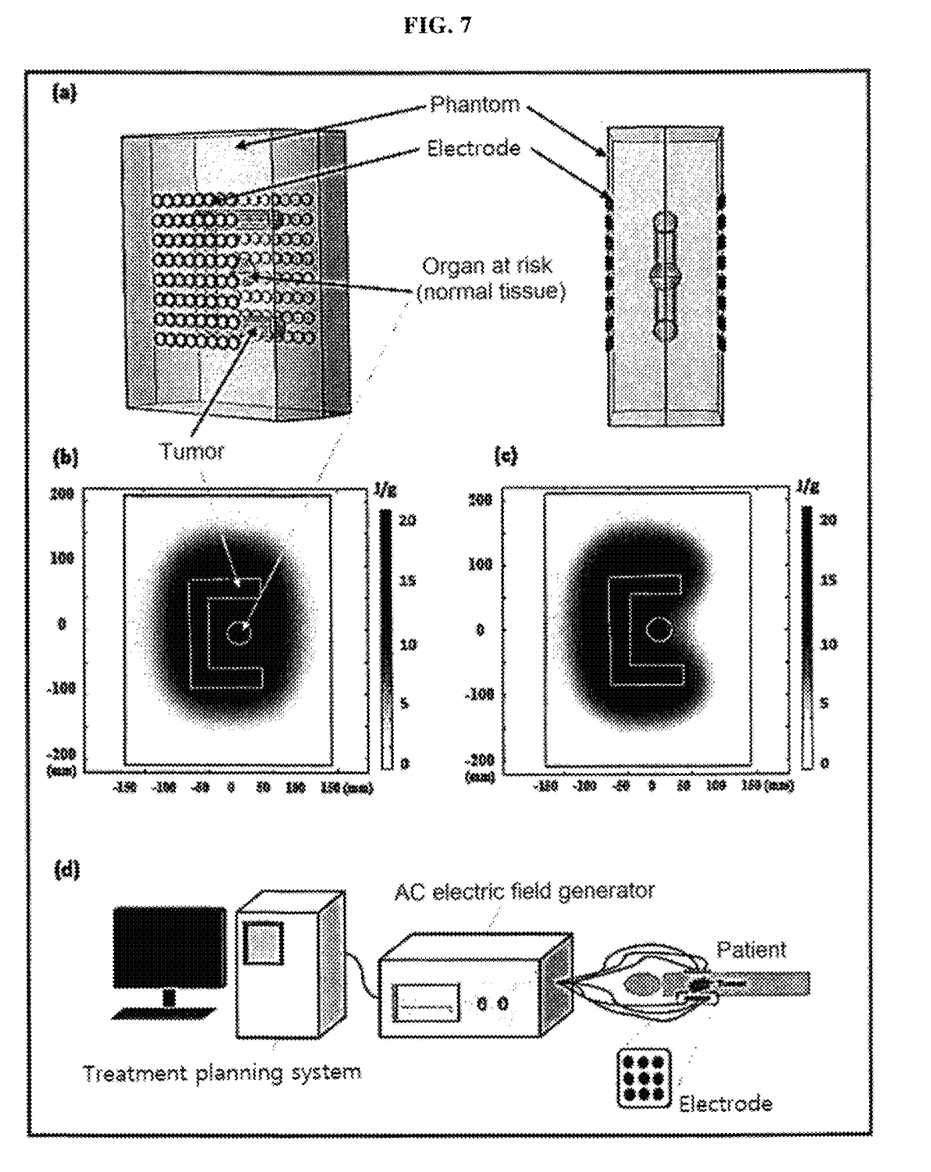
FIG. 7 is a diagram showing the results of dose optimization performed using the absorbed energy based dose unit in the electric field treatment for a tumor tissue phantom and normal cells in an organ at risk in a human model phantom.

FIG. 7 shows the results of dose optimization for electric field treatment performed using an absorbed energy based dose unit for a human model phantom that included tumor tissue and an organ at risk containing normal cells. FIG. 7(a) shows the phantom including the tumor tissue and the organ at risk; FIG. 7(b) shows the dose distribution before dose optimization; FIG. 7(c) shows the dose distribution after dose optimization; and FIG. 7(d) shows an electric field cancer treatment system linked to a system for planning electric field cancer treatment according to an embodiment of the present disclosure.

The ⊏-shaped tumor and the spherical organ of normal tissues at risk in the human model phantom were set, and alternating current electric fields of 200 kHz were applied (FIG. 7(a)).

Dose distributions in the tumor and the organ at risk were evaluated before (FIG. 7(b)) and after (FIG. 7(c)) the dose optimization process in the body shown in FIG. 6. Before the optimization process, the specific energy absorbed applied to both the tumor and the organ at risk was ~ 20 J/g. After the optimization process, however the specific energy absorbed applied to the tumor was 20 J/g, whereas the specific energy absorbed applied to the organ at risk was 10-15 J/g, showing that the optimization process could lower the specific energy absorbed that was applied to the organ at risk.

Figure 8:
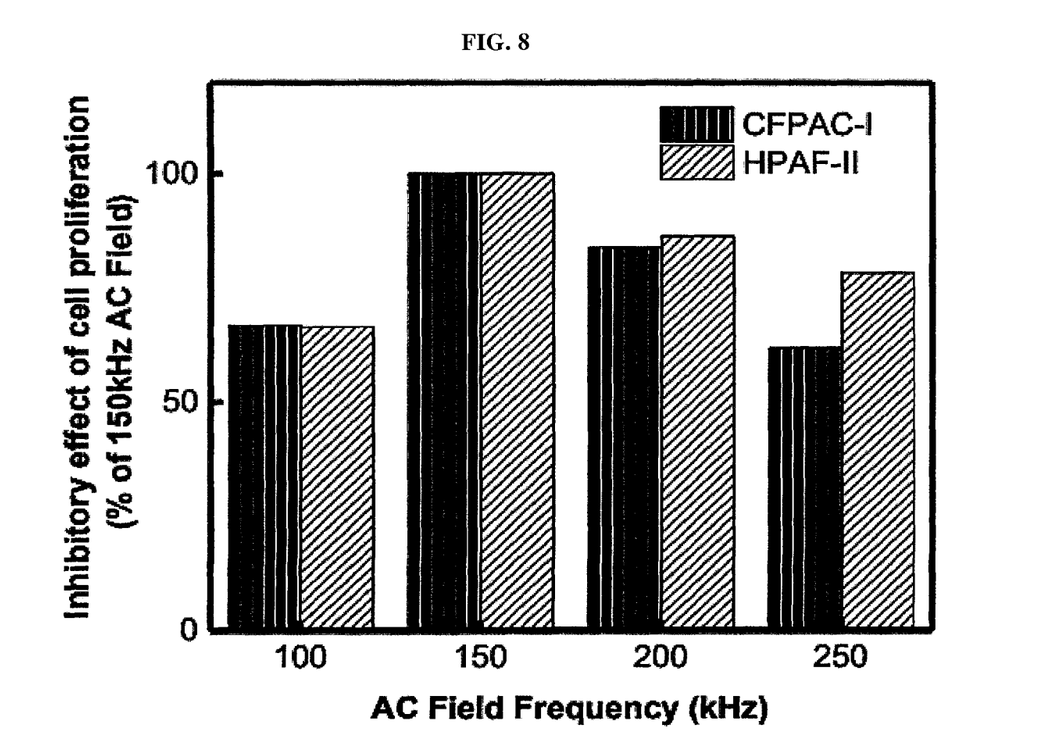
FIG. 8 is a diagram showing that inhibition by electric fields of cell proliferation was dependent on the electric field frequency.

FIG. 8 shows that the ability of electric fields to inhibit cell proliferation was dependent on the electric field frequency. Electric fields of intensity of about 1.2 V/cm but different frequencies were applied to the pancreatic cancer cell lines CFPAC-I and HPAF-II for 48 hours and cell proliferation was assessed, with inhibition expressed as a percentage relative to a frequency of 150 kHz. FIG. 8 shows that, at equivalent electric field intensity and duration, the biological effects of absorbed energy transmitted to the cells were dependent on frequency. Specifically, these experiments showed that cell proliferation was inhibited most effectively at 150 kHz, with exposure to electric fields at a frequency of 100 kHz having an inhibitory effect on cell proliferation of only about 60-70% when compared with treatment at a frequency of 150 kHz. The dependence on frequency is a general phenomenon, occurring not only in pancreatic cancer cells but in all types of cells (Non-Patent Literature 7).

Thus, when determining a prescribed dose for a specific type of cancer based on absorbed energy, it is desirable to set frequency (i.e., a reference frequency) as a criterion. If frequencies other than the reference frequency are used, it is necessary to correct the prescribed dose by applying the corresponding frequency weighting factor. For example, when a prescribed dose is based on a reference frequency of 100 J/g and the frequency weighting factor of the usage frequency is 2.0, it is necessary to correct the prescribed dose to 200 J/g. This frequency weighting factor can be calculated using Equation 4, below, and the prescribed dose at the usage frequency may be corrected using Equation 5.

Frequency weighting factor (usage frequency)=Inhibitory effect of cell proliferation (reference frequency)/Inhibitory effect of cell proliferation (usage frequency)  [Equation 4]

Prescribed dose (usage frequency)=Prescribed dose (reference frequency)×Frequency weighting factor  [Equation 5]

Figure 9:
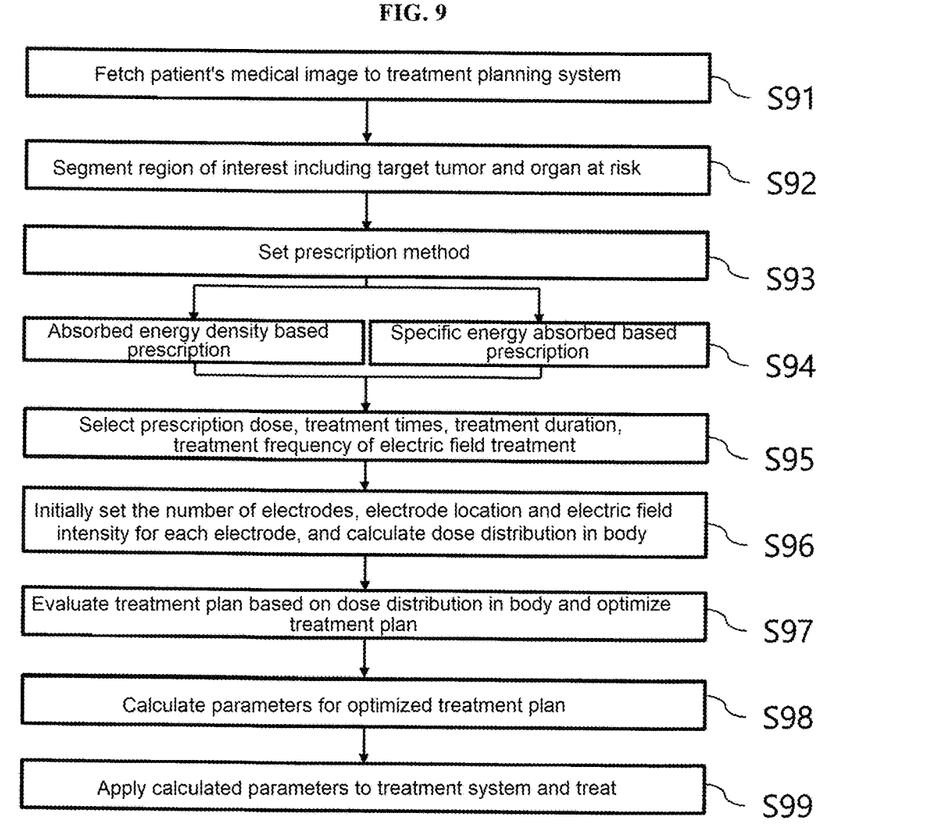
FIG. 9 is a flowchart of a method for planning electric field cancer treatment according to an embodiment of the present disclosure.

FIG. 9 is a flowchart of a method for planning electric field cancer treatment according to an embodiment of the present disclosure. Initially, a patient's medical image (for example, 3D medical image data) may be retrieved by the treatment planning system (S91) and an ROI including a target tumor and an organ at risk may be segmented (S92). Subsequently, a prescription method may be set based on an absorbed energy density based approach or a specific energy absorbed based approach (S93, S94), and prescription information, including prescribed dose, treatment times, treatment duration and treatment frequency, may be determined according to the set prescription method (S95).

Based on this method, the number and location of electrodes, as well as the electric field intensity for each electrode, are initially set, taking into account the location of the tumor and the organs at risk near the tumor. Dose distributions throughout the body may be calculated based on these settings (S96).

Subsequently, a treatment plan may be evaluated based on the calculated dose distribution in the body, and a process for optimizing the treatment plan may be utilized, as described above (FIG. 6) (S97). The parameters for the optimized treatment plan are calculated (S98), and electric field treatment may be performed by applying the calculated parameters to the treatment system (S99).

According to an embodiment of the present disclosure as described above, it is possible to provide patients with more reasonable and efficient treatments than the existing electric field treatment method performed without a special treatment planning system. In practice, this method allows for the individualized treatment of each patient and maximizes the inhibition of cell proliferation.

Figure 10:
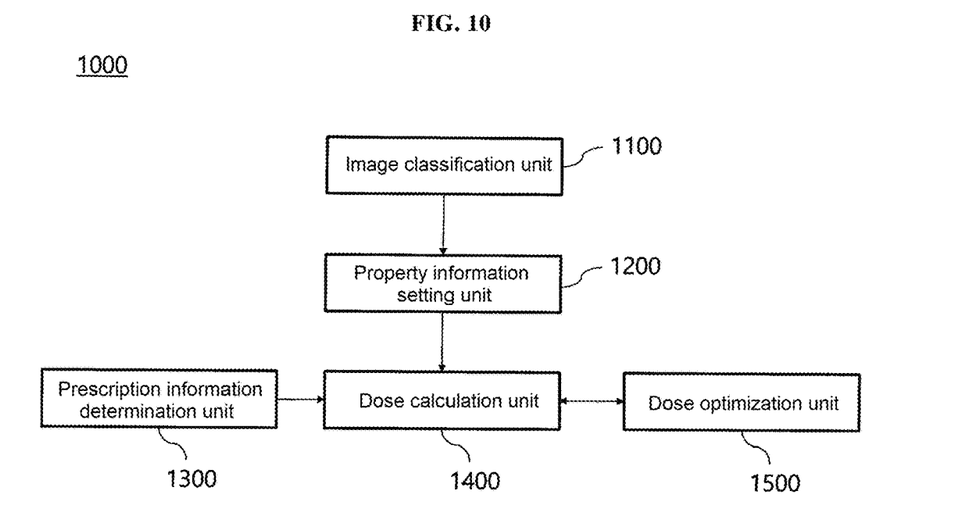
FIG. 10 is a diagram showing a system for planning electric field cancer treatment according to another embodiment of the present disclosure.

FIG. 10 shows an architectural diagram of a system for planning electric field cancer treatment according to another embodiment of the present disclosure. System 1000 for planning electric field cancer treatment may include an image classification unit 1100, a property information setting unit 1200, a prescription information determination unit 1300, a dose calculation unit 1400 and a dose optimization unit 1500.

The image classification unit 1100 may receive a patient's medical image as input that includes an organ and a tumor and can classify the organ and tumor. For example, the image classification unit 1100 may classify a tumor and each organ from a patient's 3D medical image, reconstruct a 3D image for each classified region and identify the positional relationships between the tumors and most organs. The property information setting unit 1200 may set the properties of each region (for example, the tumor, the organ and other human tissues) classified by the image classification unit 1100. In this example, the property information may include the electrical conductivity and mass density of each tissue in the human body. The electrical conductivity may be set based on magnetic resonance imaging (MRI) or a pre-constructed database of the electrical conductivity of each human tissue. Additionally, the mass density may be set based on computed tomography (CT) or a pre-constructed database of mass density of each human tissue.

The prescription information determination unit 1300 may set a prescription method, taking into account the input tumor type and conditions, and determine prescription information, including prescribed doses, treatment times, treatment duration and treatment frequency. The prescription method may be an absorbed energy density based approach or a specific energy absorbed based approach, with the units of the prescribed doses determined accordingly.

In addition, the prescribed dose may be determined by a method involving the absorbed energy transmitted to the tissues at a preset reference frequency. When the treatment frequency differs from the reference frequency, the prescribed dose may be corrected by applying a frequency weighting factor that reflects the biological effect of frequency.

The dose calculation unit 1400 may initially set the number and location of electrodes, as well as the electric field intensity for each electrode, taking into account the location of each region (for example, tumors, organs and other tissues in the human body) classified by the image classification unit 1100. Based on these findings, the dose calculation unit 1400 can calculate the dose distribution in the body based on the settings. These dose distributions may be absorbed energy density or specific energy absorbed distributions, depending on the set prescription method, with these distributions calculated according Equations 2 and 3, respectively.

The dose optimization unit 1500 may optimize the dose by changing at least one electrode in an electrode pad utilized as equipment for electric field cancer treatment. This unit may alter the location or electric field intensity of each electrode, such that the maximum prescribed dose is delivered to the tumor and minimal doses are delivered to the surrounding normal tissues.

For example, the dose optimization unit 1500 may set the number of electrodes and the electrode location, based on the dose distribution in the body calculated by the dose calculation unit 1400. The dose optimization unit 1500 may determine the size of the electrode pad and optimize the dose by repeating the process of changing the arrangement of electrodes or the electric field intensity of each electrode (i.e., the voltage applied to each electrode).

The present disclosure is not limited to the above-described embodiments and the accompanying drawings. As will be obvious to those skilled in this field, substitutions, modifications and changes may be made to the elements of the present disclosure without departing from its technical spirit.

The invention claimed is:

1. A system for planning electric field cancer treatment based on absorbed energy, comprising:
   an image classification unit to classify a patient's medical image into an organ and a tumor;
   a property information setting unit to set property information for each region classified by the image classification unit;
   a prescription information determination unit to set a prescription method, taking into account input type and condition information of the tumor, and determine prescription information including prescribed dose, treatment times, treatment duration and treatment frequency;
   a dose calculation unit to initially set the number and location of electrodes used for electric field cancer treatment, as well as the electric field intensity for each electrode, taking into account the location of each region classified by the image classification unit, and calculate the dose distribution in the body based on the initial settings; and
   a dose optimization unit to optimize the dose by changing the number, location, or electric field intensity of at least one electrode, such that the maximal prescribed dose is delivered to the tumor and a minimal dose is delivered to surrounding normal tissues,
   wherein the prescription method is any type of absorbed energy density based approach or specific energy absorbed based approach, and the unit of the prescribed dose is determined as any unit of absorbed energy density or specific energy absorbed according to the set prescription method.

2. The system for planning electric field cancer treatment based on absorbed energy of claim 1, wherein the property information includes electrical conductivity and mass density of each tissue in human body.

3. The system for planning electric field cancer treatment based on absorbed energy of claim 2, wherein the electrical conductivity is set based on magnetic resonance imaging (MRI) or a pre-constructed database of electrical conductivity of each human tissue.

4. The system for planning electric field cancer treatment based on absorbed energy of claim 2, wherein the mass density is set based on computed tomography (CT) or a pre-constructed database of mass density of each human tissue.

5. The system for planning electric field cancer treatment based on absorbed energy of claim 1, wherein the absorbed energy density is calculated according to the Equation:

$$\text{absorbed energy density} = \text{power loss density} \times \text{electric field duration}.$$

6. The system for planning electric field cancer treatment based on absorbed energy of claim 1, wherein the specific energy absorbed is calculated according to the Equation:

$$\text{specific energy absorbed} = (\text{power loss density} \times \text{electric field duration}) \div (\text{mass density}).$$

7. The system for planning electric field cancer treatment based on absorbed energy of claim 1, wherein the prescription information determination unit determines the prescribed dose by absorbed energy transmitted to tissues at a preset reference frequency.

8. The system for planning electric field cancer treatment based on absorbed energy of claim 7, wherein the prescription information determination unit corrects the prescribed dose by applying a frequency weighting factor to reflect the biological effect of frequency when the treatment frequency is different from the reference frequency.

9. A method for planning electric field cancer treatment based on absorbed energy, comprising:
   segmenting a region of interest that includes a tumor and an organ in a patient's medical image;
   setting a prescription method based on any type of absorbed energy density or specific energy absorbed based approach;
   determining prescription information including prescribed dose, treatment times, treatment duration and treatment frequency according to the set prescription method;
   calculating dose distribution in the body based on the initially set number and location of electrodes, and the electric field intensity for each electrode, considering both the tumor and the organ; and
   evaluating and optimizing a treatment plan based on the calculated dose distribution in the body,
   wherein the absorbed energy density is calculated according to the Equation:

$$\text{absorbed energy density} = \text{power loss density} \times \text{electric field duration}.$$

10. A method for planning electric field cancer treatment based on absorbed energy, comprising:
    segmenting a region of interest that includes a tumor and an organ in a patient's medical image;
    setting a prescription method based on any type of absorbed energy density or specific energy absorbed based approach;
    determining prescription information including prescribed dose, treatment times, treatment duration and treatment frequency according to the set prescription method;
    calculating dose distribution in the body based on the initially set number and location of electrodes, and the electric field intensity for each electrode, considering both the tumor and the organ; and
    evaluating and optimizing a treatment plan based on the calculated dose distribution in the body,
    wherein the specific energy absorbed is calculated according to the Equation:

$$\text{specific energy absorbed} = (\text{power loss density} \times \text{electric field duration}) \div (\text{mass density}).$$

11. A system for planning electric field cancer treatment based on absorbed energy, comprising:
- an image classification unit classifying a patient's medical image into an organ and a tumor;
- a property information setting unit setting property information for each region classified by the image classification unit;
- a prescription information determination unit setting a prescription method, and determining prescription information including prescribed dose, treatment times, treatment duration and treatment frequency;
- a dose calculation unit initially setting the number and location of electrodes used for electric field cancer treatment, as well as the electric field intensity for each electrode, and calculating the dose distribution in the body based on the initial settings; and
- a dose optimization unit optimizing the dose by changing the number, location, or electric field intensity of at least one electrode, wherein the prescription method is any type of absorbed energy density based approach or specific energy absorbed based approach, and the unit of the prescribed dose is determined as any unit of absorbed energy density or specific energy absorbed according to the set prescription method.

12. The system for planning electric field cancer treatment based on absorbed energy of claim 11, wherein the absorbed energy density is calculated according to the Equation:

$$\text{absorbed energy density} = \text{power loss density} \times \text{electric field duration}.$$

13. The system for planning electric field cancer treatment based on absorbed energy of claim 11, wherein the specific energy absorbed is calculated according to the Equation:

$$\text{specific energy absorbed} = (\text{power loss density} \times \text{electric field duration}) \div (\text{mass density}).$$

* * * * *